United States Patent [19]
Tachikawa et al.

[11] Patent Number: 6,111,126
[45] Date of Patent: Aug. 29, 2000

[54] METHOD FOR SYNTHESIZING ORGANOSILICON COMPOUNDS THAT CONTAIN A FUNCTIONAL GROUP BONDED TO SILICON ACROSS THE SI-C BOND

[75] Inventors: Mamoru Tachikawa; Kasumi Takei, both of Kanagawa, Japan

[73] Assignee: Dow Corning Asia, Ltd., Tokyo, Japan

[21] Appl. No.: 09/452,506

[22] Filed: Dec. 1, 1999

[30] Foreign Application Priority Data

Dec. 1, 1998 [JP] Japan .................................. 10-341716

[51] Int. Cl.$^7$ ....................................................... C07F 7/08
[52] U.S. Cl. ......................... 556/479; 532/440; 532/445; 532/450; 532/453; 549/215
[58] Field of Search ..................... 556/479, 440, 556/445, 450, 453; 549/215

[56] References Cited

U.S. PATENT DOCUMENTS

| | | | |
|---|---|---|---|
| 5,424,470 | 6/1995 | Bank et al. | 556/479 |
| 5,481,016 | 1/1996 | Bank et al. | 556/479 |
| 5,486,637 | 1/1996 | Bank et al. | 556/479 |

*Primary Examiner*—Paul F. Shaver
*Attorney, Agent, or Firm*—Melvin D. Fletcher

[57] ABSTRACT

A method for synthesizing organosilicon compounds that contain a functional group bonded to silicon across the Si—C bond. The method comprises reacting an unsaturated group-functional organic compound or unsaturated group-functional organosilicon compound with a hydro(hydrocarbonoxy)silane compound, where the reaction is carried out in the presence of a platinum catalyst.

21 Claims, No Drawings

METHOD FOR SYNTHESIZING ORGANOSILICON COMPOUNDS THAT CONTAIN A FUNCTIONAL GROUP BONDED TO SILICON ACROSS THE SI-C BOND

BACKGROUND OF INVENTION

The invention is a method for synthesizing organosilicon compounds that contain a functional group bonded to silicon across the Si—C bond. The method comprises reacting an unsaturated group-functional organic compound or unsaturated group-functional organosilicon compound with a hydro(hydrocarbonoxy)silane compound, where the reaction is carried out in the presence of a platinum catalyst.

The hydrosilylation reaction is a method for the chemical modification of organic compounds by silane compounds. This method employs hydrosilylation between SiH-functional silane and an unsaturated bond-bearing organic compound and is applicable to a broad range of SiH-functional compounds and unsaturated bond-bearing organic compounds. Platinum and rhodium catalysts are generally used to run the hydrosilylation reaction in the industrial or commercial sphere. Since these metals are very expensive, it is crucial that the catalytic efficiency in the hydrosilylation reaction also be very high. In addition, the hydrosilylation reaction is frequently accompanied by competing side reactions and may itself include reaction pathways that produce a number of isomers. As a consequence, the hydrosilylation reaction is generally accompanied by such catalyst-related issues as product yield, product selectivity, and production of a single isomer. Modification of the catalyst can be carried out in order to address these problems and issues. For example, various ligands can be added and/or chemically bonded to the catalyst, or the catalyst can be immobilized on any of various different supports. However, these chemical and physical modifications themselves are typically problematic, for example, their effects may rapidly disappear and an improved catalytic selectivity is generally accompanied by a lower activity. In addition, since platinum catalysts gradually lose their activity under oxygen-free conditions, implementation of the hydrosilylation reaction in the presence of oxygen becomes unavoidable notwithstanding the concomitant induction of side reactions and risk of fire.

The object of the present invention is to introduce a reaction method that provides a high catalyst activity and stability and that also provides a high positional selectivity in the hydrosilylation reaction product. An additional object is to achieve these features without the addition of oxygen and thereby reduce the risk of fire and explosion in the hydrosilylation reaction.

SUMMARY OF INVENTION

The present invention is a method for synthesizing organosilicon compounds that contain a functional group bonded to silicon across the Si—C bond. The method comprises reacting an unsaturated group-functional organic compound or unsaturated group-functional organosilicon compound with a hydro(hydrocarbonoxy)silane compound defined by formula $$(2) \ HR^2{}_m Si(OR^3)_{3-m} \quad (2),$$

where m=0, 1, or 2; each $R^2$ is independently selected from organic groups containing from 1 to 10 carbons; and each $R^3$ is independently selected from hydrocarbon groups containing from 1 to 10 carbons, the reaction is carried out in the presence of a hydro(acyloxy)silane compound defined by formula (1)

$$HSiR_n(O(C=O)R^1)_{3-n} \quad (1),$$

where n=0, 1, or 2; each R is independently selected from organic groups, siloxy groups, and siloxanoxy groups; and each $R^1$ is independently selected from the hydrogen atom and organic groups, where the reaction is carried out in the presence of a platinum catalyst.

No specific restrictions apply in the present invention to the particular combination of the hydro(acyloxy)silane compound (1) $HSiR_n(O(C=O)R^1)_{3-n}$ and hydro(hydrocarbonoxy)silane compound (2) $HR^2{}_m Si(OR^3)_{3-m}$. For example, the H $R^2{}_m Si(OR^3)_{3-m}$ submitted to reaction in the presence of $HSi(O(C=O)R^1)_3$ can be freely selected from $HSi(OR^3)_3$, when m=0, $HR^2Si(OR^3)_2$, when m=1, and $HR^2{}_2Si(OR^3)$, when m=2. The same applies to $HSiR(O(C=O)R^1)_2$ and $HSiR_2(O(C=O)R^1)$.

Examples of the unsaturated group-functional organic compound and unsaturated group-functional organosilicon compounds are styrene and styrene derivatives; vinylsilane compounds; siloxane compounds containing the vinyl group directly bonded to silicon; epoxy-functional olefins; diene compounds; allyl compounds defined by $CH_2=CHCH_2X$ where X=halogen, alkoxy, or acyloxy; vinyl-terminate olefin compounds; and acetylenic compounds.

The reactivity with the hydro(hydrocarbonoxy)silane compound is not substantially impaired, the unsaturated compound may contain atoms other than carbon and hydrogen in its structure, said other atoms being selected from O, N, F, Cl, Br, Si, and S. However, the allyl compounds remain as previously defined.

The styrene and styrene derivatives can be exemplified by styrenic hydrocarbons such as p-methylstyrene, p-ethylstyrene, p-phenylstyrene, and divinylbenzene; halogenated styrenes such as p-fluorostyrene, p-chlorostyrene, p-bromostyrene, p-iodostyrene, p-(chloromethyl)styrene, and m-(chloromethyl)styrene; oxygenated styrene derivatives and silicon-containing styrene derivatives such as p-methoxystyrene and p-trimethylsilylstyrene; nitrogenous styrene derivatives such as p-(diphenylamino)styrene, p-(ditolylamino)styrene, p-(dixylylamino)styrene, and bis(4-vinylphenyl)(4-methylphenyl)amine.

The vinylsilane compounds and siloxane compounds containing the vinyl group directly bonded to silicon can be exemplified by vinyltrialkylsilanes such as vinyltrimethylsilane, vinyltriethylsilane, vinyltripropylsilane, and vinyldimethylethylsilane; vinylalkoxysilanes such as vinyltrimethoxysilane, vinyltriethoxysilane, vinylmethyldiethoxysilane, and vinyldimethylmethoxysilane; vinyl-functional siloxanes such as 1,3-divinyltetramethyldisiloxane, α,ω-divinylpolydimethylsiloxanes, and 1,3,5,7-tetravinyl-1,3,5,7-tetramethylcyclotetrasiloxane; and vinyl-functional silazanes such as 1,3-divinyltetramethyldisilazane and 1,3,5,7-tetravinyl-1,3,5,7-tetramethylcyclotetrasilazane.

The epoxy-functional olefins can be exemplified by allyl glycidyl ether and vinylcyclohexene oxide. The diene compounds can be exemplified by 1,3-butadiene, isoprene, 1,5-hexadiene, 1,3-octadiene, and 1,3-cyclohexadiene. The allyl compound $CH_2=CHCH_2X$ can be exemplified by allyl chloride, allyl acetate, and allyl methacrylate.

The vinyl-terminated olefin compounds may be straight chain or branched and may contain an aromatic hydrocarbon group as a substituent. The straight-chain terminally unsaturated olefin compounds can be exemplified by ethylene, propylene, 1-butene, 1-hexene, 1-octene, and 1-octadecene. The branched terminally unsaturated olefin compounds can be exemplified by isobutylene, 3-methyl-1-butene, 3,5-dimethyl-1-hexene, and 4-ethyl-1-octene.

Olefin compounds containing a selection or selections from O, N, F, Cl, Br, Si, and S can be exemplified by oxygenated allyl compounds such as allyl methacrylate; vinyl-functional amine compounds such as N-vinylcarbazole; halogenated olefins such as 4-chloro-1-butene and 6-bromo-1-hexene; Si-functional olefin compounds such as allyloxytrimethylsilane; and sulfur-containing olefin compounds such as allyl mercaptan and allyl sulfide. Allylbenzene and 4-phenyl-1-butene are examples of aromatic hydrocarbon group-containing olefin compounds.

The acetylenic compound may contain the terminal ethynyl group (CH≡C—) or may contain the ethynylene group —C≡C—) in internal position in the molecule. The acetylenic compound can also contain aromatic hydrocarbyl as a substituent.

The following are examples of the acetylenic compound having the terminal ethynyl group —CH≡C—: acetylene, propyne, 1-butyne, 1-hexyne, and 1-octyne. The following are examples of the acetylenic compound having the ethynylene –C≡C- group in internal position in the molecule: 2-butyne, 2-hexyne, 3-hexyne, and 4-octyne. The aromatic hydrocarbyl-substituted acetylenic compound can be exemplified by phenylacetylene, 3-phenylpropyne, and 4-phenyl-1-butyne. Acetylenic compounds containing a selection or selections from O, N, F, Cl, Br, Si, and S can be exemplified by oxygenated acetylenic compounds such as 3-methyl-1-butyn-3-ol and 3-phenyl-1-butyn-3-ol; silicon-containing acetylenic compounds such as O-trimethylsilylated 3-methyl-1-butyn-3-ol (HC≡C—C(CH$_3$)$_2$—O—Si(CH$_3$)$_3$) and O-trimethylsilylated 3-phenyl-1-butyn-3-ol (HC≡C—C(CH$_3$)(C$_6$H$_5$)—O—Si(CH$_3$)$_3$); and halogenated acetylenic compounds such as propargyl chloride and propargyl bromide.

The hydro(hydrocarbonoxy)silane compound used in the present invention defined by formula (2) HSiR$^2_m$(OR$^3$)$_{3-m}$ (2) and is a silicon compound that contains hydrogen directly bonded to the silicon atom and that also contains at least 1 hydrocarbonoxy group OR$^3$ bonded to the same silicon atom. When multiple hydrocarbonoxy groups are present, the hydrocarbonoxy groups bonded to the single silicon atom may differ from one another. R$^3$ in formula (2) represents hydrocarbon groups that contain from 1 to 10 carbon atoms. Each R$^2$ in formula (2) is independently selected from organic groups that contain from 1 to 10 carbon atoms. R$^2$ is preferably selected from hydrocarbon groups that contain from 1 to 10 carbons, and hydrocarbon groups that contain a heteroatom or heteroatoms in addition to carbon and hydrogen and that contain a total of 1 to 10 carbons. The heteroatom can be, for example, a selection from O, N, S, F, Cl, Br, I, and Si. The heteroatom may be present in the hydrocarbon group in terminal or pendant position or may be present within the main chain skeleton itself.

When m=2, the hydrocarbon groups R$^2$ bonded to the single silicon atom may differ from one another. Among the hydrocarbon groups described above, R$^2$ is preferably alkyl. R$^2$ can be exemplified by the examples provided above for R$^3$ and also by chloromethyl, 4-chlorophenyl, trimethylsilylmethyl, and 2-methoxyethyl. R$^3$ can be exemplified by alkyl such as methyl, ethyl, n-propyl, isopropyl, n-butyl, tert-butyl, pentyl, hexyl, octyl, and decyl; alkenyl such as 2-propenyl, hexenyl, and octenyl; aralkyl such as benzyl and phenethyl; and aryl such as phenyl, tolyl, and xylyl.

The hydro(hydrocarbonoxy)silane compound can be specifically exemplified by the following but is not limited to or by these examples: trihydrocarbonoxysilanes such as trialkoxysilanes, trialkenoxysilanes, and triaryloxysilanes, and specifically trimethoxysilane, triethoxysilane, tri-n-propoxysilane, triisopropoxysilane, tributoxysilane, triisopropenoxysilane, and triphenoxysilane; dihydrocarbonoxysilanes such as dialkoxysilanes, dialkenoxysilanes, and diaryloxysilanes, and specifically methyldimethoxysilane, methyldiethoxysilane, methyldi-n-propoxysilane, methyldiisopropenoxysilane, methyldiphenoxysilane, ethyldimethoxysilane, ethyldiethoxysilane, n-propyldimethoxysilane, n-propyldiethoxysilane, methyldioctyloxysilane, 3,3,3-trifluoropropyldimethoxysilane, 3,3,3-trifluoropropyldiethoxysilane, n-hexyldimethoxysilane, n-hexyldiethoxysilane, n-octyldimethoxysilane, n-octyldiethoxysilane, benzyldimethoxysilane, benzyldiethoxysilane, phenethyldimethoxysilane, phenethyldiethoxysilane, phenyldimethoxysilane, and phenyldiethoxysilane; and monohydrocarbonoxysilanes such as monoalkoxysilanes, monoalkenoxysilanes, and monoaryloxysilanes, and specifically dimethylmethoxysilane, dimethylethoxysilane, dimethyl-n-propoxysilane, dimethylisopropenoxysilane, dimethylphenoxysilane, diethylmethoxysilane, methylethylethoxysilane, n-propyl(methyl)methoxysilane, n-propyl(methyl)ethoxysilane, 3,3,3-trifluoropropyl(methyl)methoxysilane, bis(3,3,3-trifluoropropyl)ethoxysilane, n-hexyl(methyl)methoxysilane, di(n-hexyl)ethoxysilane, n-octyl(methyl)methoxysilane, di(n-octyl)ethoxysilane, benzyl(methyl)methoxysilane, phenethyl(methyl)methoxysilane, and methylphenylmethoxysilane. The following are examples of hydrocarbonoxysilane that contains two or more different hydrocarbonoxy groups selected from alkoxy, alkenoxy, aralkyloxy, and aryloxy: methoxydiethoxysilane, diethoxypropenoxysilane, dimethoxyphenoxysilane, dimethoxybenzyloxysilane, diphenoxypropenoxysilane, and methylmethoxyphenethoxysilane. The silane compound under consideration can also be exemplified by the preceding compounds in which R has been replaced by, for example, chloromethyl, 4-chlorophenyl, trimethylsilylmethyl, and 2-methoxyethyl.

The hydro(hydrocarbonoxy)silane compound should be selected as a function of its reactivity or the intended application of the hydrocarbonoxysilyl-functional polymer that will be produced. In general, use of the alkoxysilane will be optimal when reactivity is a primary consideration.

The hydro(hydrocarbonoxy)silane compound may be used in the reaction under consideration in an amount equal to the unsaturated group present in the unsaturated compound, but can be added in excess from 1.1 gram-equivalents to 100 gram-equivalents per 1 mole unsaturated group in the unsaturated compound for the purposes of running the reaction faster and to completion with the excess being removed post-reaction.

The hydro(acyloxy)silane compound used by the present invention has the formula (1)

where R is preferably selected from $C_1$ to $C_6$ hydrocarbyl and $C_1$ to $C_6$ alkoxy and R$^1$ is preferably hydrogen or a saturated or unsaturated hydrocarbon group that contains from 1 to 20 carbons and that may contain at least 1 atom selected from oxygen, halogen, sulfur, and silicon.

The group R can be exemplified by methyl, ethyl, n-propyl, isopropyl, phenyl, methoxy, ethoxy, n-propoxy, and isopropoxy. The group R$^1$ can be exemplified by hydrogen, methyl, ethyl, n-propyl, isopropyl, and phenyl.

The hydro(acyloxy)silane compound used by the present invention can be exemplified by hydroformyloxysilanes, hydroacetoxysilanes, hydropropionyloxysilanes, hydrobutyryloxysilanes, hydrolauroyloxysilanes, hydrostearoyloxysilanes, hydrobenzoyloxysilanes, hydrochloroacetoxysilanes, hydrodichloroacetoxysilanes, hydrotrichloroacetoxysilanes, hydrotrifluoroacetoxysilanes, and hydrobenzyloylsilanes. The hydro(acyloxy)silane can be exemplified by hydroformyloxysilanes such as dimethylformyloxysilane, diethylformyloxysilane, methylphenylformyloxysilane, methylmethoxyformyloxysilane, methylethoxyformyloxysilane, methylisopropoxyformyloxysilane, and diphenylformyloxysilane; hydroacetoxysilanes such as dimethylacetoxysilane, diethylacetoxysilane, methylphenylacetoxysilane, methylmethoxyacetoxysilane, methylethoxyacetoxysilane, methylisopropoxyacetoxysilane, and diphenylacetoxysilane; hydropropionyloxysilanes such as dimethylpropionyloxysilane, diethylpropionyloxysilane, methylphenylpropionyloxysilane, methylmethoxypropionyloxysilane, methylethoxypropionyloxysilane, methylisopropoxypropionyloxysilane, and diphenylpropionyloxysilane; hydrobutyryloxysilanes such as dimethylbutyryloxysilane, diethylbutyryloxysilane, methylphenylbutyryloxysilane, methylmethoxybutyryloxysilane, methylethoxybutyryloxysilane, methylisopropoxybutyrylsilane, and diphenylbutyryloxysilane; hydrolauroyloxysilanes such as dimethyllauroyloxysilane, methylphenyllauroyloxysilane, diphenyllauroyloxysilane, methylmethoxylauroyloxysilane, and methylethoxylauroyloxysilane; hydrostearoyloxysilanes such as dimethylstearoyloxysilane, methylphenylstearoyloxysilane, diphenylstearoyloxysilane, methylmethoxystearoyloxysilane, and methylethoxystearoyloxysilane; hydrobenzoyloxysilanes such as dimethylbenzoyloxysilane, methylphenylbenzoyloxysilane, diphenylbenzoyloxysilane, methylmethoxybenzoyloxysilane, and methylethoxybenzoyloxysilane; hydrochloroacetoxysilanes such as dimethylchloroacetoxysilane, methylphenylchloroacetoxysilane, diphenylchloroacetoxysilane, methylmethoxychloroacetoxysilane, and methylethoxychloroacetoxysilane; hydrodichloroacetoxysilanes such as dimethyldichloroacetoxysilane, methylphenyldichloroacetoxysilane, diphenyldichloroacetoxysilane, methylmethoxydichloroacetoxysilane, and methylethoxydichloroacetoxysilane; hydrotrichloroacetoxysilanes such as methylphenyltrichloroacetoxysilane, diphenyltrichloroacetoxysilane, methylmethoxytrichloroacetoxysilane, and methylethoxytrichloroacetoxysilane; hydrotrifluoroacetoxysilanes such as dimethyltrifluoroacetoxysilane, methylphenyltrifluoroacetoxysilane, diphenyltrifluoroacetoxysilane, methylmethoxytrifluoroacetoxysilane, and methylethoxytrifluoroacetoxysilane.

The hydro(acyloxy)silane compound can be effectively used at an addition that gives from 0.001 weight % to 20 weight % in the reaction system, but is preferably added at from 0.01 weight % to 5 weight % in order to use this component efficiently while still obtaining higher levels of desirable activity. Here, the reaction system refers to the mixture of the hydro(acyloxy)silane compound, plus unsaturated compound, plus hydro(hydrocarbonoxy)silane compound, plus platinum catalyst used in the preparative method according to the present invention.

The platinum catalyst can be exemplified by platinum and its compounds. More specifically, the platinum catalyst can be selected from the negatively-charged complexes of platinum; compounds of zero-valent, divalent, and tetravalent platinum; and colloidal platinum. The negatively-charged complexes of platinum can be exemplified by platinum-carbonyl cluster anions such as $[Pt_3(CO)_6]^{2-}$, $[Pt_3(CO)_6]_2^{2-}$, and $[Pt_3(CO)_6]_4^{2-}$; zero-valent platinum compounds such as the platinum(0)-divinyltetramethyldisiloxane complex, the platinum(0)-tetravinyltetramethylcyclotetrasiloxane complex, platinum (0)-ethylene complexes, and platinum(0)-styrene complexes; divalent-platinum compounds such as $Pt(II)Cl_2$, $Pt(II)Br_2$, bis(ethylene)$Pt(II)Cl_2$, (1,5-cyclooctadiene)$Pt(II)Cl_2$, platinum(II) acetylacetonate, and bis(benzonitrile)$Pt(II)Cl_2$; and tetravalent-platinum compounds such as $Pt(IV)Cl_4$, $H_2Pt(IV)Cl_6$, $Na_2Pt(IV)Cl_6$, and $K_2Pt(IV)Cl_2$. The platinum (0)-divinyltetramethyldisiloxane complex and alcohol solutions of chloroplatinic acid are particularly preferred. The amount of platinum required for the hydrosilylation of a certain amount of substrate is related, inter alia, to such factors as the type of substrate, reaction temperature, and reaction time and hence cannot be uniformly or universally specified. In general, however, the platinum can be used at from $10^{-3}$ to $10^{-8}$ mole platinum per 1 mole substrate hydro(hydrocarbonoxy)silane compound and, when factors such as catalyst economics and reaction time are considered, the use of $10^{-4}$ to $10^{-7}$ mole will be more suitable.

The reaction temperature should be from 10° C. to 250° C. The range from 20° C. to 200° C. is optimal based on such considerations as achieving a suitable reaction rate, product stability, and stability of the substrate participating in the reaction.

The use of solvent in the method is not absolutely necessary, but a hydrocarbon compound can be used as a reaction solvent or as a solvent for the catalyst component for such purposes as dissolving the substrate, facilitating control of the temperature in the reaction system, and facilitating addition of the catalyst component. Solvents optimal for these purposes are saturated and unsaturated hydrocarbon compounds, for example, hexane, cyclohexane, heptane, octane, dodecane, benzene, toluene, xylene, and dodecylbenzene; and halogenated hydrocarbons such as chloroform, methylene chloride, chlorobenzene, and ortho-dichlorobenzene.

The invention will be explained in greater detail by the examples, but this invention is not limited to or by these examples.

GC stands for gas chromatography in the descriptions of product characterization in the examples that follow. Otherwise, Et is an abbreviation for the ethyl group, OAc is an abbreviation for the acetoxy group, and Ph is an abbreviation for the phenyl group.

The acyloxysilane, alkylsilane, and siloxane compounds used in the examples were either obtained by purchase or were synthesized by known methods. The unsaturated compounds were obtained by purchase and were used as obtained.

Reference Example. Synthesis of methylethoxyacetoxysilane ($HSi(CH_3)(OEt)(OAc)$). Methyldiethoxysilane (2.7 g) and methyldiacetoxysilane (3.2 g) were mixed in a nitrogen atmosphere and were then held at room temperature for several hours. Analysis of the resulting mixture by GC and proton-NMR showed the production of methylethoxyacetoxysilane as the main component, approximately 90%, along with methyldiethoxysilane, approximately 5%, and methyldiacetoxysilane, approximately 5%.

Example 1. The platinum-catalyzed reaction of α,ω-divinylpolydimethylsiloxane with dimethylethoxysilane in the presence of dimethylacetoxysilane. A 800 mg sample of α,ω-divinylpolydimethylsiloxane, degree of polymerization=approximately 9, and 208 mg of dimethylethoxysilane, HSi(CH$_3$)$_2$OEt, (2 mmoles) were placed in a glass reaction tube. This was followed by the addition of dimethylacetoxysilane, HSi(CH$_3$)$_2$OAc, (28 mg) and then the addition of 0.002 mL of a toluene solution (platinum content=0.04 wt %) of a zero-valent platinum complex with divinylsiloxane. The reaction tube was subsequently sealed with Teflon™ tape, placed in an oil bath heated to 50° C., and heated for 1 hour. After cooling, the contents were analyzed by proton-NMR, which showed that the vinyl in the α,ω-divinylpolydimethylsiloxane were completely hydrosilylated and that the α-adduct: β-adduct ratio for the dimethylethoxysilyl group to the vinyl group was 1:101.

Comparative Example 1. The platinum-catalyzed reaction of α,ω-divinylpolydimethylsiloxane with dimethylethoxysilane in the absence of a hydro(acyloxy)silane compound. A 725 mg sample of α,ω-divinylpolydimethylsiloxane (degree of polymerization=approximately 9) and 208 mg of dimethylethoxysilane, HSi(CH$_3$)$_2$OEt, (2 mmoles) were placed in a glass reaction tube. This was followed by the addition of 0.002 mL of a toluene solution (platinum content=0.04 wt %) of a zero-valent platinum complex with divinylsiloxane. The reaction tube was then sealed with Teflon™ tape, placed in an oil bath heated to 50° C., and heated for 1 hour. After cooling, the contents were analyzed by proton-NMR, which showed that the vinyl in the α,ωdivinylpolydimethylsiloxane were completely hydrosilylated and that the α-adduct: β-adduct ratio for the dimethylethoxysilyl group to the vinyl group was 1:7.8.

Example 2. The platinum-catalyzed reaction of styrene and dimethylethoxysilane in the presence of dimethylacetoxysilane. A 233 mg sample of styrene (2.2 mmoles) and 208 mg of dimethylethoxysilane. HSi(CH$_3$)$_2$OEt, (2 mmoles) were placed in a glass reaction tube. This was followed by the addition of dimethylacetoxysilane, HSi(CH$_3$)$_2$OAc, (28 mg) and then the addition of 0.002 mL of a toluene solution (platinum content=0.04 wt %) of a zero-valent platinum complex with divinylsiloxane.

The reaction tube was subsequently sealed with Teflon™ tape, placed in an oil bath heated to 50° C., and heated for 1 hour. After cooling, the contents were analyzed by GC (FID), which showed a 33% conversion of the vinyl group in the styrene with the production of PhC$_2$H$_4$Si(CH$_3$)$_2$(OEt) in a yield of 28% and PhC$_2$H$_4$Si(CH$_3$)$_2$(OAc) in a yield of 3.4%. The α-adduct: β-adduct ratio for the PhC$_2$H$_4$Si(CH$_3$)$_2$(OEt) was 1:153.

Comparative Example 2. The platinum-catalyzed reaction of styrene and dimethylethoxysilane in the absence of a hydro(acyloxy)silane compound. A 208 mg sample of styrene (2 mmoles) and 208 mg of dimethylethoxysilane HSi(CH$_3$)$_2$OEt, (2 mmoles) were placed in a glass reaction tube. This was followed by the addition of 0.002 mL of a toluene solution (platinum content=0.04 wt %) of a zero-valent platinum complex with divinylsiloxane. The reaction tube was subsequently sealed with Teflon™ tape, placed in an oil bath heated to 50° C., and heated for 1 hour. After cooling, the contents were analyzed by GC (FID), which showed a 31% conversion of the vinyl group in the styrene with the production of PhC$_2$H$_4$Si(CH$_3$)$_2$(OEt) in a yield of 29%. The α-adduct: β-adduct ratio for the PhC$_2$H$_4$Si(CH$_3$)$_2$(OEt) was 1:4.0.

Example 3. The platinum-catalyzed reaction of 1-octene with dimethylethoxysilane in the presence of dimethylacetoxysilane. A 590 mg sample of 1-octene and 415 mg of dimethylethoxysilane HSi(CH$_3$)$_2$OEt, (4 mmoles) were placed in a glass reaction tube. This was followed by the addition of dimethylacetoxysilane, HSi(CH$_3$)$_2$OAc, (56 mg, 0.4 mmole) and then the addition of 0.001 mL of a toluene solution (platinum content=0.04 wt %) of a zero-valent platinum complex with divinylsiloxane. The reaction tube was subsequently sealed with Teflon™ tape, placed in an oil bath heated to 50° C., and heated for 1 hour. After cooling, the contents were analyzed by GC (FID), which showed a 77% conversion of the 1-octene with the production of n-octyldimethylethoxysilane in a yield of 70% and n-octyldimethylacetoxysilane in a yield of 5.5%.

Comparative Example 3. The platinum-catalyzed reaction of 1-octene with dimethylethoxysilane in the absence of a hydro(acyloxy)silane compound. A 450 mg sample of 1-octene and 215 mg of dimethylethoxysilane HSi(CH$_3$)$_2$OEt, (4 mmoles) were placed in a glass reaction tube. This was followed by the addition of 0.001 mL of a toluene solution (platinum content=0.04 wt %) of a zero-valent platinum complex with divinylsiloxane. The reaction tube was subsequently sealed with Teflon™ tape, placed in an oil bath heated to 50° C., and heated for 1 hour. After cooling, the contents were analyzed by GC (FID), which showed a 21% conversion of the 1-octene with the production of n-octyldimethylethoxysilane in a yield of 20%.

Example 4. The platinum-catalyzed reaction of α,ω-divinylpolydimethylsiloxane with methyldiethoxysilane, HSi(CH$_3$)OEt$_2$ in the presence of methyl(ethoxy) acetoxysilane. A 816 mg sample of α,ω-divinylpolydimethylsiloxane (degree of polymerization=9) and 277 mg of methyldiethoxysilane (2 mmoles) were placed in a glass reaction tube. This was followed by the addition of methyl(ethoxy)acetoxysilane, HSi(CH$_3$)(OEt) OAc, (26 mg, 0.2 mmole) and then the addition of 0.001 mL of a toluene solution (platinum content=0.4 wt %) of a zero-valent platinum complex with divinylsiloxane. The reaction tube was subsequently sealed with Teflon™ tape, placed in an oil bath heated to 80° C., and heated for 1 hour. After cooling, the contents were analyzed by proton-NMR, which showed that the vinyl in the α,ω-divinylpolydimethylsiloxane was completely hydrosilylated and that the α-adduct: β-adduct ratio for the methyldiethoxysilyl group to the vinyl group was 1:63.

Comparative Example 4. The platinum-catalyzed reaction of α,ω-divinylpolydimethylsiloxane with methyldiethoxysilane in the absence of a hydro(acyloxy)silane compound. A 727 mg sample α,ω-divinylpolydimethylsiloxane (degree of polymerization=9) and 288 mg of methyldiethoxysilane, HSi(CH$_3$)OEt$_2$, (2 mmoles) were placed in a glass reaction tube. This was followed by the addition of 0.001 mL of a toluene solution (platinum content=0.4 wt %) of a zero-valent platinum complex with divinylsiloxane. The reaction tube was subsequently sealed with Teflon™ tape, placed in an oil bath heated to 80° C., and heated for 1 hour. After cooling, the contents were analyzed by proton-NMR, which showed that approximately 95% of the vinyl in the α,ω-divinylpolydimethylsiloxane had been hydrosilylated and that the α-adduct: β-adduct ratio for the methyldiethoxysilyl group to the vinyl group was 1:4.7.

Example 5. The platinum-catalyzed reaction of styrene and methyldiethoxysilane in the presence of methyldiacetoxysilane. A 232 mg sample of styrene (2.2 mmoles) and 282 mg of methyldiethoxysilane, HSi(CH$_3$)OEt$_2$, (2.1 mmoles) were placed in a glass reaction tube. This was followed by the addition of methyldiacetoxysilane, HSi(CH$_3$)OAc)$_2$, (16 mg, 0.1 mmole) and then the addition of 0.001 mL of a toluene solution (platinum content=0.4 wt %) of a zero-valent platinum complex with divinylsiloxane. The reaction tube was subsequently sealed with Teflon™ tape, placed in an oil bath heated to 80° C., and heated for 1 hour. After cooling, analysis of the contents by GC showed an approximately 93% conversion of the vinyl group in the styrene. The yields of the hydrosilylates were 83% phenethylmethyldiethoxysilane and 6.5% phenethylmethylethoxyacetoxysilane. Ethanol (30 mg) was then added to the reaction solution and the reaction solution was allowed to stand for 30 minutes. Analysis of the resulting reaction solution by GC showed that the phenethylmethylethoxyacetoxysilane had disappeared and the phenethylmethyldiethoxysilane had increased to approximately 90%. This shows that the Si-bonded acyloxy group can be easily converted to alkoxy by reaction with alcohol with a corresponding improvement in the yield of the alkoxysilane compound and depletion of the acyloxysilane compound. The α-phenethyl adduct: β-phenethyl adduct ratio was 1:37.

Comparative Example 5. The platinum-catalyzed reaction of styrene and methyldiethoxysilane in the absence of a hydro(acyloxy)silane compound. A 212 mg sample of styrene (2 mmoles) and 279 mg of methyldiethoxysilane (HSi(CH$_3$)(OEt)$_2$, 2.1 mmoles) were placed in a glass reaction tube. This was followed by the addition of 0.001 mL of a toluene solution (platinum content=0.4 wt %) of a zero-valent platinum complex with divinylsiloxane. The reaction tube was subsequently sealed with Teflon™ tape, placed in an oil bath heated to 80° C., and heated for 1 hour. After cooling, analysis of the contents by gas chromatography showed an approximately 65% conversion of the vinyl group in the styrene. The hydrosilylate yield was 63% phenethylmethyldiethoxysilane. The α-phenethyl adduct: β-phenethyl adduct ratio was 1:1.65.

We claim:

1. A method for synthesizing organosilicon compounds that contain a functional group bonded to silicon across the Si—C bond comprising:

reacting an unsaturated group-functional organic compound or unsaturated group-functional organosilicon compound with a hydro(hydrocarbonoxy)silane compound defined by formula (2)

HR$^2_m$Si(OR$^3$)$_{3-m}$ (2), where m=0, 1, or 2; each R$^2$ is independently selected from organic groups containing from 1 to 10 carbons; and each R$^3$ is independently selected from hydrocarbon groups containing from 1 to 10 carbons, the reaction is carried out in the presence of a hydro(acyloxy)silane compound defined by formula (1)

HSiR$_n$(O(C=O)R$^1$)$_{3-n}$ (1), where n=0, 1, or 2; each R is independently selected from organic groups, siloxy groups, and siloxanoxy groups; and each R$^1$ is independently selected from the hydrogen atom and organic groups, where the reaction is carried out in the presence of a platinum catalyst.

2. A method according to claim 1, wherein the unsaturated group-functional organic compound and the unsaturated group-functional organosilicon compound are selected from the group consisting of styrene and styrene derivatives; vinylsilane compounds; siloxane compounds containing the vinyl group directly bonded to silicon; epoxy-functional olefins; diene compounds; allyl compounds defined by CH$_2$=CHCH$_2$X where X=halogen, alkoxy, or acyloxy; vinyl-terminated olefin compounds; and acetylenic compounds.

3. A method according to claim 1, wherein the hydro(acyloxy)silane compound is represented by formula (1), where R is a substituent selected from hydrocarbon groups having from 1 to 6 carbon atoms and alkoxy groups having from 1 to 6 carbon atoms and R$^1$ is a substituent selected from the hydrogen atom and saturated and unsaturated hydrocarbon groups that contain from 1 to 20 carbons and that may contain at least 1 atom selected from oxygen, halogen, sulfur, and silicon.

4. A method according to claim 2, wherein the hydro(acyloxy)silane compound is represented by formula (1), where R is a substituent selected from hydrocarbon groups having from 1 to 6 carbon atoms and alkoxy groups having from 1 to 6 carbon atoms and R$^1$ is a substituent selected from the hydrogen atom and saturated and unsaturated hydrocarbon groups that contain from 1 to 20 carbons and that may contain at least 1 atom selected from oxygen, halogen, sulfur, and silicon.

5. A method according to claim 1, wherein the unsaturated group-functional organic compound or unsaturated group-functional organosilicon compound is α,ω-divinylpolydimethylsiloxane, the hydro(hydrocarbonoxy)silane compound is dimethylethoxysilane and the hydro(acyloxy)silane compound is dimethylacetoxysilane.

6. A method according to claim 5, wherein the unsaturated group-functional organic compound or unsaturated group-functional organosilicon compound is styrene.

7. A method according to claim 5, wherein the unsaturated group-functional organic compound or unsaturated group-functional organosilicon compound is 1-octene.

8. A method according to claim 1, wherein the unsaturated group-functional organic compound or unsaturated group-functional organosilicon compound is α,ω-divinylpolydimethylsiloxane, the hydro(hydrocarbonoxy)silane compound is methyldiethoxysilane and the hydro(acyloxy)silane compound is methyl(ethoxy)acetoxysilane.

9. A method according to claim 1, wherein the unsaturated group-functional organic compound or unsaturated group-functional organosilicon compound is styrene, the hydro(hydrocarbonoxy)silane compound is methyldiethoxysilane and the hydro(acyloxy)silane compound is methyldiacetoxysilane.

10. A method according to claim 1, wherein the amount of the hydro(acyloxy)silane compound is 0.001 weight % to 20 weight %.

11. A method according to claim 1, wherein the amount of the hydro(acyloxy)silane compound is 0.01 weight % to 5 weight %.

12. A method according to claim 1, wherein the amount of the hydro(hydrocarbonoxy)silane compound is equal to the unsaturated group present in he unsaturated compound.

13. A method according to claim 1, wherein the amount of the hydro(hydrocarbonoxy)silane compound is in excess from 1.1 gram-equivalents to 100 gram-equivalents per 1 mole unsaturated group in the unsaturated compound.

14. A method according to claim 1, wherein the reaction is carried out at a temperature in the range of from 10° C. to 250° C.

15. A method according to claim 1, wherein the reaction is carried out at a temperature in the range of from 20° C. to 200° C.

16. A method according to claim 1, wherein the platinum catalyst is a zero-valent platinum complex with divinylsiloxane.

17. A method according to claim 5, wherein the platinum catalyst is a zero-valent platinum complex with divinylsiloxane.

18. A method according to claim 6, wherein the platinum catalyst is a zero-valent platinum complex with divinylsiloxane.

19. A method according to claim 7, wherein the platinum catalyst is a zero-valent platinum complex with divinylsiloxane.

20. A method according to claim 8, wherein the platinum catalyst is a zero-valent platinum complex with divinylsiloxane.

21. A method according to claim 9, wherein the platinum catalyst is a zero-valent platinum complex with divinylsiloxane.

* * * * *